(12) United States Patent
Roy

(10) Patent No.: US 8,452,391 B2
(45) Date of Patent: May 28, 2013

(54) OCULAR IONTOPHORESIS DEVICE

(75) Inventor: Pierre Roy, Paris (FR)

(73) Assignee: EyeGate Pharma S.A.S. (FR)

( * ) Notice: Subject to any disclaimer, the term of this patent is extended or adjusted under 35 U.S.C. 154(b) by 0 days.

(21) Appl. No.: 13/326,843

(22) Filed: Dec. 15, 2011

(65) Prior Publication Data
US 2012/0089077 A1 Apr. 12, 2012

Related U.S. Application Data

(63) Continuation of application No. 11/297,942, filed on Dec. 9, 2005, now Pat. No. 8,099,162.

(60) Provisional application No. 60/740,592, filed on Nov. 29, 2005.

(51) Int. Cl.
*A61N 1/30* (2006.01)

(52) U.S. Cl.
USPC ............ 604/20; 604/294; 604/295; 604/300; 604/301; 604/521

(58) Field of Classification Search
USPC .................. 604/20, 289, 294, 295, 300, 301, 604/501, 521
See application file for complete search history.

(56) References Cited

U.S. PATENT DOCUMENTS

| 2,525,381 | A | 10/1950 | Tower |
| 6,154,671 | A | 11/2000 | Parel et al. |
| 6,319,240 | B1 | 11/2001 | Beck |
| 2002/0016575 | A1 | 2/2002 | Beck et al. |
| 2002/0107508 | A1* | 8/2002 | Burnett ............................ 606/5 |
| 2005/0182351 | A1 | 8/2005 | Henley et al. |
| 2005/0245856 | A1 | 11/2005 | Roy |

FOREIGN PATENT DOCUMENTS

WO 0062857 10/2000

OTHER PUBLICATIONS

Monti et al.; Effect of Iontophoresis on Transcorneal Permeation 'In Vitro' of Two Beta-Blocking Agents, and on Corneal Hydration; International Journal of Pharmaceutics; vol. 250; Issue 2; pp. 423-429; Jan. 16, 2003.

* cited by examiner

*Primary Examiner* — Emily Schmidt
(74) *Attorney, Agent, or Firm* — Pierce Atwood LLP; Joseph M. Maraia

(57) ABSTRACT

The invention relates to a device of ocular iontophoresis for delivering active substances, comprising a reservoir having an outer wall and a hollow body at least partly delimited by the outer wall, wherein the hollow body is capable of receiving an electrical conductive medium and active substances contained in the medium and has an outlet defining a surface, so-called "application surface", intended to received a determine part of an eyeball surface, the application surface being at least partly limited by an outer line concave towards the optical axis of the eyeball, wherein the outer wall extends from the outer line with a global outwardly with respect to the said optical axis.

16 Claims, 6 Drawing Sheets

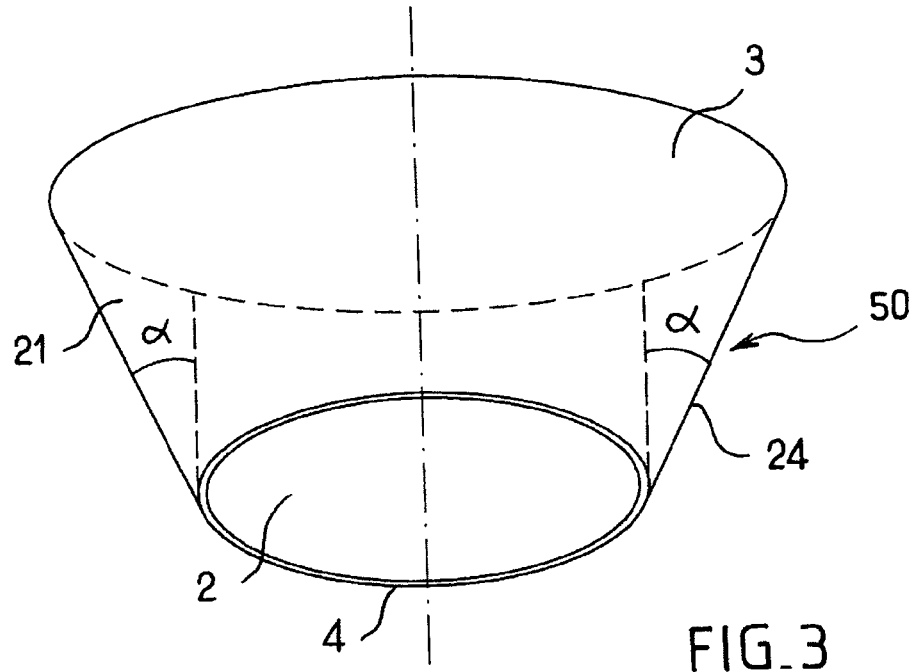
FIG_3
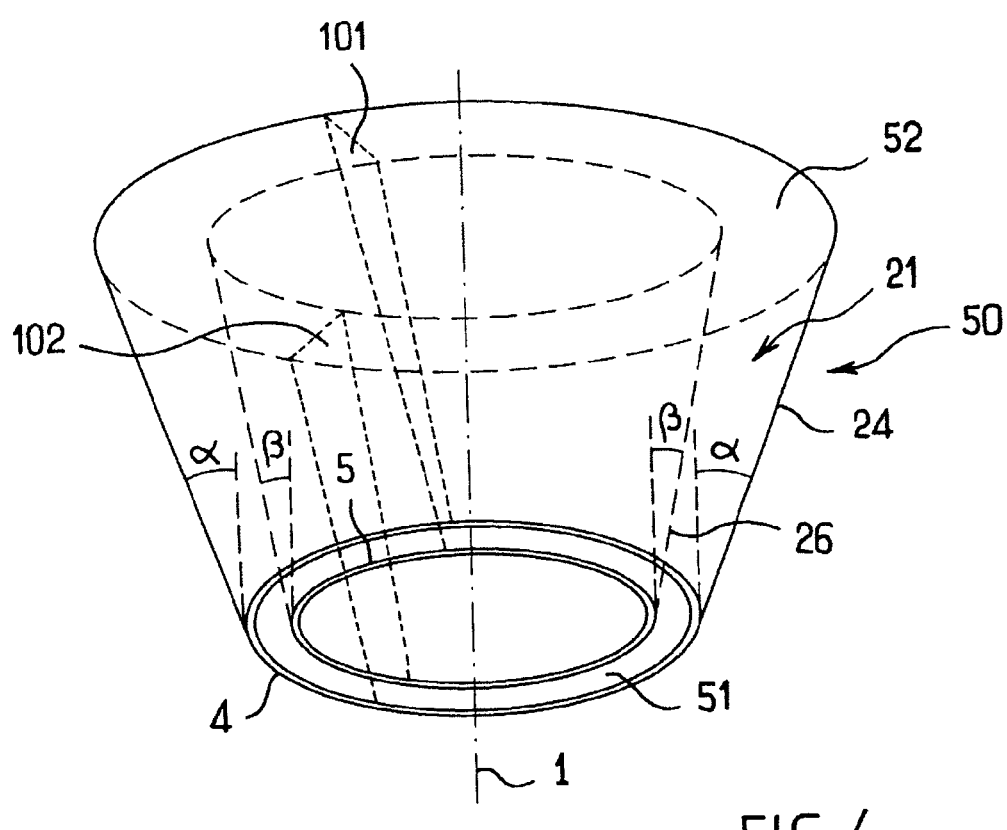
FIG_4

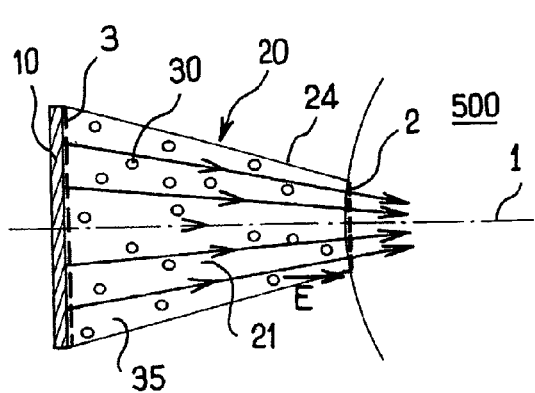
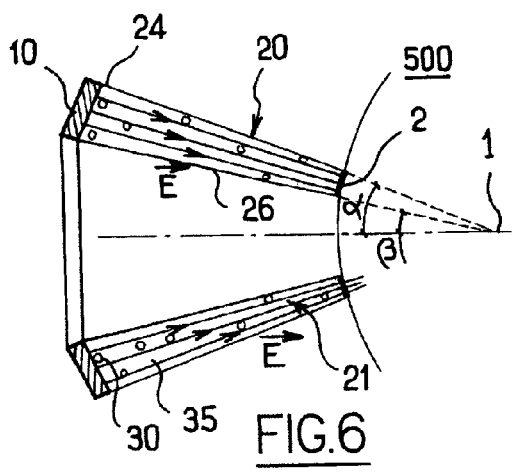
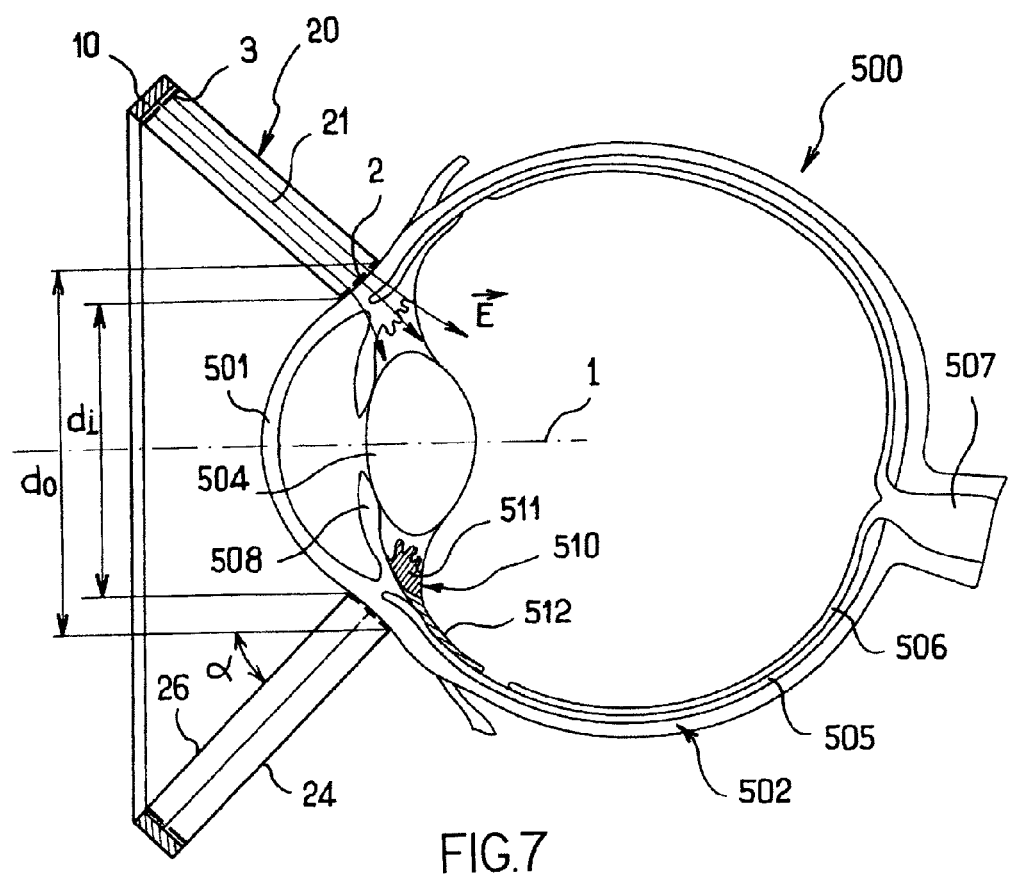

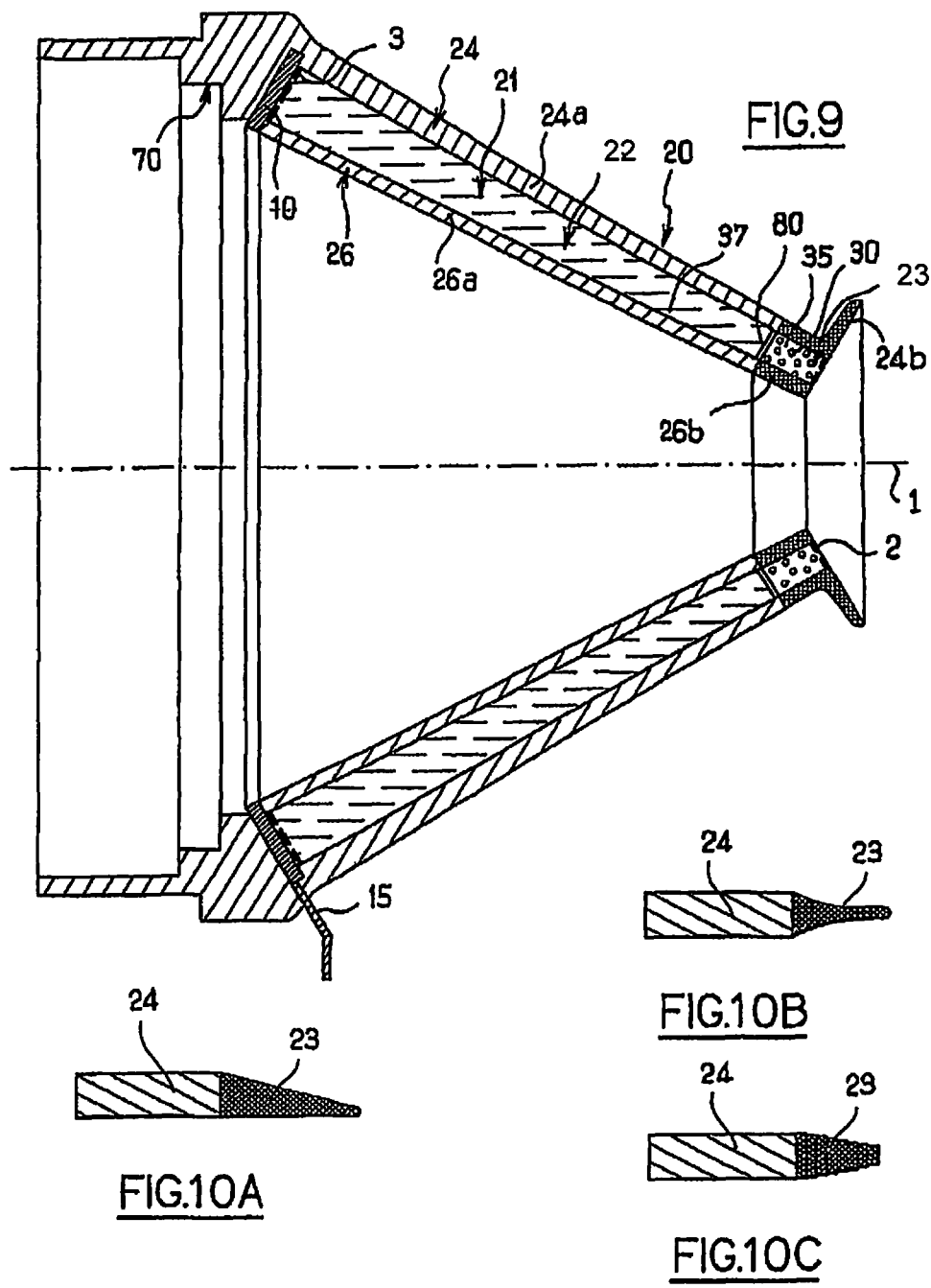

OCULAR IONTOPHORESIS DEVICE

This application is a continuation of U.S. patent application Ser. No. 11/297,942, filed Dec. 9, 2005, now U.S. Pat. No. 8,099,162, which claims the benefit of the filing date of U.S. Provisional Application No. 60/740,592, entitled Ocular Iontophoresis Device, filed Nov. 29, 2005, the disclosure of which is hereby incorporated herein by reference.

TECHNICAL FIELD

The invention relates to the delivery of medication to ocular tissues by iontophoresis.

Ocular iontophoresis consists typically of applying an electric field to active substances in order to guide them, once ionized, into determinate target ocular tissues. To this aim, a first electrode, so-called as "active" electrode, applies an electric field to an electrical conductive medium containing the active principles placed adjacent to the eye, and a second electrode, so-called "passive" electrode, serves as a return electrode enabling the electric circuit to be looped through the patient's body.

The iontophoresis technique is then a non-invasive technique, which overcomes the drawbacks of previous techniques of delivering substances into the eye, such as topical delivery by eye drops (inefficient in most of therapeutics applications); injections around the eye (traumatic, risking infection, bleeding, cataracts, retina detachment, involving rapid dilution); inserts—like lenses or conjunctival sacs—in the form of reservoirs of medication placed on the ocular surface (need a long-term ocular tolerance, risk of expelling, patient compliance); intraocular implants (need of surgery, expensive treatment, need a regular replacement, no possibility of tapering or accelerating the treatment once implanted).

TECHNICAL BACKGROUND

U.S. Pat. No. 3,122,137 describes a iontophoresis applicator applied on the orbit and not on the eye's surface and incorporating the current source. It does not propose means for keeping the eye's open and it is believed a large part of the product is also delivered into systemic circulation, due to a lack of precision in the placement of the device.

Iontophoresis devices in U.S. Pat. No. 5,522,864 and U.S. Pat. No. 6,101,411 should suffer from the same drawbacks.

U.S. Pat. No. 4,564,016 discloses a device having a small application surface (diameter 1 mm), applied on sclera and allowing very high current densities (between 50 and 2000 mA/cm2) for "focal iontophoresis". These values should be toxic for concerned tissues, as confirmed in Maurice article in Ophthalmology (January 1986, vol 93, number 1) entitled <<Iontophoresis of fluorescing into the posterior segment of the rabbit eye>>.

Last, U.S. Pat. No. 6,154,671, discloses the principle of a device for delivering all kinds of active substances with safety and accuracy by iontophoresis, and answers then to most of the problematic of iontophoresis for ophthalmology.

More recently, U.S. Pat. No. 6,319,240 proposes an improvement of previous methods with a sealed reservoir applied on sclera (with a semi-permeable membrane on application face) under the eyelid. The semi-permeable membrane of this device is supposed to limit arcing effect between the electrode and the eye's surface that could occur due to the limited thickness and small surface of the device.

U.S. Pat. No. 6,442,423 describes a device where the product is cast in a gel and applied on cornea.

All the previous devices are implemented for delivering substances through the cornea or the sclera, in order to reach some determinate tissues.

Nevertheless, there is a need to improve the efficiency and decrease the time of application of some therapies implemented by iontophoresis.

For example, the therapy of glaucoma by iontophoresis needs to be improved.

Glaucoma is characterized by elevated intraocular pressure (IOP also known as ocular hypertension).

Glaucoma is classified as "open-angle glaucoma", which results from decreased permeability of the aqueous humor through the trabecular meshwork, or as "angle-closure glaucoma" that results from shifting of the iris forward so that the anterior chamber angle is obstructed or congenital.

The congenital form of glaucoma rarely responds to therapy and is more commonly treated with surgery, but not by iontophoresis means.

It is known that elevated IOP can be at least partially controlled by administering drugs which either reduce the production of aqueous humor within the eye, such as beta-blockers or carbonic anhydrase inhibitors, or increase the outflow of aqueous humor from the eye, such as miotics or sympathomimetics.

These pharmacological approaches help restore the IOP to a normotensive state either by inhibiting the production of aqueous humor by the ciliary body, or facilitating trabecular or uveoscleral aqueous humor outflow.

To this aim, most of the drugs are administered topically (eye drops) to avoid associated systemic effects.

Although a wide variety of pharmaceutical treatments for lowering IOP are available for the glaucoma patient, these treatments are then limited either in terms of efficiency or side-effects.

Additionally, the previous iontophoresis devices are not specifically arranged for treating glaucoma.

A first object of the invention is to provide an ocular iontophoresis device which leads to an increase of the concentration of drugs delivered into the intraocular tissue, improving for example the treatment of glaucoma.

Another object of the invention is to reach the first object by providing a iontophoresis device arranged for decreasing the loss of medication before reaching the targeted tissues by limiting the risks of absorptions of the medication by intermediates and/or by increasing the guiding of the ionized medication, for then more sufficiently treating intraocular tissues.

Another object of the invention is to decrease the time necessary for administrating a determinate amount of substances while administering the same amount of active substances.

BRIEF DESCRIPTION OF THE INVENTION

The present invention attempts to reach these purposes by proposing, according to a first aspect, a device of ocular iontophoresis for delivering active substances, comprising a reservoir having an outer wall and a hollow body at least partly delimited by the outer wall, wherein the hollow body is capable of receiving an electrical conductive medium and active substances contained in the medium and has an outlet defining a surface, so-called "application surface", intended to receive a determine part of an eyeball surface, the application surface being at least partly limited by an outer line concave towards the optical axis of the eyeball, wherein the outer wall extends from the outer line globally outwardly with respect to the said optical axis.

According to a second aspect, the invention proposes a device of ocular iontophoresis for delivering active substances, comprising a reservoir and an active electrode, wherein the reservoir has a hollow body capable of receiving an electrical conductive medium and active substances contained in the medium, the hollow body having a first end and a second end, the first end being an outlet defining a surface, so-called "application surface", intended to receive a determine part of an eyeball surface, and the second end is opposite the first end, defining then the bottom of the reservoir, wherein at least one wall delimiting the hollow body extends from the application surface to the bottom such that the area of the bottom is greater than the area of the application surface, wherein the active electrode is associated with the reservoir so as to, when polarized, supply an electric field through the medium to the eyeball, the active electrode extending proximate to the bottom of the reservoir and having a global area greater than area of the application surface.

BRIEF DESCRIPTION OF THE FIGURES

Other characteristics, objects, and advantages of the invention appear clearer in reading the description below, which is illustrated by the following figures:

FIG. 3 shows a perspective view of a device according to a first embodiment of the invention.

FIG. 4 shows a perspective view of a device according to a second embodiment of the invention.

FIG. 5 shows a longitudinal cross section of the device according to the first embodiment once applied on the eyeball.

FIG. 6 shows a longitudinal cross section of the device according to the second embodiment once applied on the eyeball.

FIG. 7 shows a longitudinal cross section of a particular device according to the second embodiment once applied on the eyeball.

FIG. 9 shows a longitudinal cross section of another particular device according to the second embodiment.

FIG. 10A to 10C show different shapes for the flexible portion of the reservoir of an ocular iontophoresis device according to the invention.

DETAILED DESCRIPTION OF THE INVENTION

Figure 1:
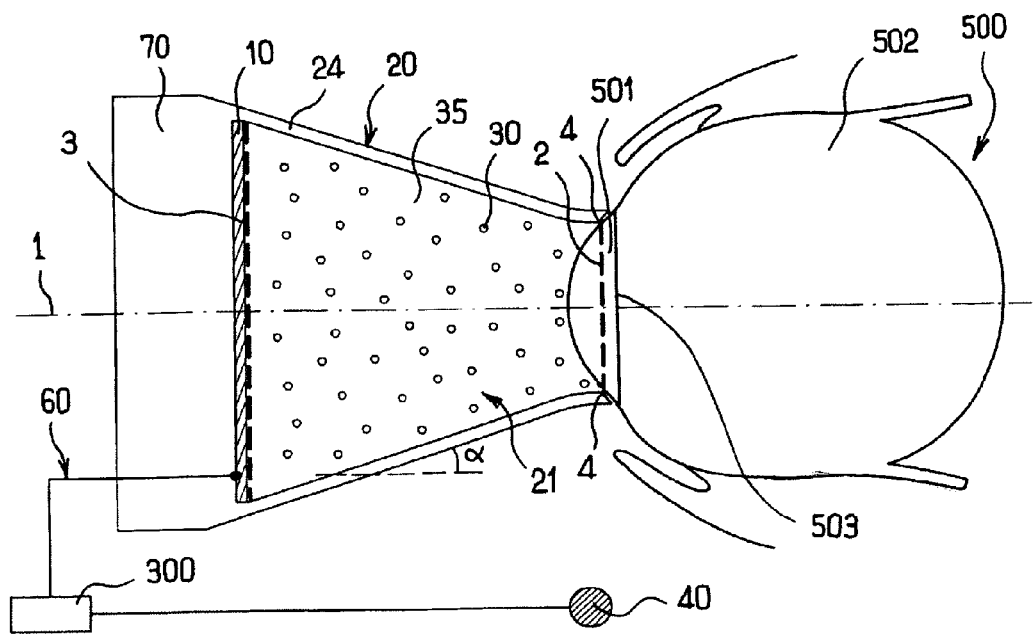
FIG. 1 shows a schematic cross-section view of a iontophoresis system according to the invention, in operation on an eyeball.

With reference to FIG. 1, an ocular iontophoresis system comprises an iontophoresis device including an active electrode 10, a reservoir 20 (defined in this device as a hollow body 21 in an outer wall 24), a rear part 70, and at least one active substance 30 contained in a medium 35 stored in the reservoir 20, and a passive electrode 40 enabling the electric circuit to be looped through the patient's body, an electrical power supply 300 delivering DC to the electrodes 10 and 40.

The power supply 300 for generating an electrical potential difference may be housed within the ocular iontophoretic device, or alternatively, may be remotely associated with the ocular iontophoretic device via conventional electrical conduit 60. Energy source preferably supplies low voltage constant direct current not exceeding 20 mA/cm$^2$ preferably not exceeding 10 mA/cm$^2$ (depending on the device's surface) for generating an electrical potential difference.

The active electrode 10 is placed proximate to the bottom 3 of the reservoir 20 either by being fitted thereto or by being formed therein directly (e.g. by electro-plating). In an alternative, the reservoir 20 and the assembly formed of the electrode 10 and the rear part 70 are different pieces, the said assembly being then placed on the reservoir 20 just before implementing iontophoresis.

The active electrode 10 can be constituted of a surface, of a wire (like a loop wire in a short circuit), of a grid or array patterned for supplying a homogeneous field, or of a surface (i.e. a film or a plate). If the active electrode 10 is constituted by a surface, its shape can be substantially the same as those of the bottom 3 of the hollow body 21 of the reservoir 20.

The active electrode 10 is placed for being in a tight electrical relation with the content of the reservoir 20. The active electrode 10 can then be situated at the bottom 3 of the reservoir 20 (see FIG. 1), or can be separated from the content of the reservoir 20 by a layer of protection formed on the electrode 10 as described in FR 2 869 531, or by an end wall provided between the active electrode 10 and the reservoir 20.

The active electrode 10 can be placed parallel to the application surface 2 of the reservoir 20, for having more efficiency on the tissues to treat.

Optionally, the electrode 10 has a predefined concave shape complementary to the eyeball's convex surface for keeping a substantially constant distance with the surface of the eyeball 500.

The active electrode 10 is advantageously arranged, in operation, to present current density of about 10 mA/cm$^2$ or less, and to be polarized for about 10 minutes or less.

The active electrode 10 may be formed directly at the bottom 3 or on an end wall of the reservoir 20. For this purpose, it is possible to use one of the following techniques:

electroplating to form the conductive layer with a conductive material to form for example a metallic film;

depositing an ink filled with an electrically conductive material in order to form the conductive layer;

depositing a solid film, of acetate for example, filled with an electrically conductive material to form the conductive layer; and overmolding polymers filled respectively with an electrically conductive material to form conductive layers.

A protective layer is optionally formed on the active electrode 10 so as to protect it or to protect the active substances 30 from metallic contaminants, as described in FR 2 869 531.

The device is advantageously arranged in such a manner that the distance between the active electrode 10 and the ocular surface is chosen so as to prevent any damage of the ocular tissue due to the electric current. Thus, this distance can be chosen about or greater than 4 mm from the ocular surface, the current of the active electrode 10 of the invention advantageously not exceeding 10 mA/cm$^2$, and the application time preferably not exceeding 10 minutes to preserve lacrymal film function.

The medium 35 housed in the reservoir 20 is preferably manufactured from a material capable of temporarily retaining the active substances 30. Medium 35 may comprise, for example, a natural or synthetic gel member, a natural or a reticulated element having a plurality of a reticulum, like synthetic foam that is geometrically and compositionally compatible for ocular applications for receiving the active substances 30 in solution, or a single solution. Electrical conductive medium, like water or hydrogel, can also be placed in the reservoir 20 in order to guide and conduct the electric field through the reservoir 20 to the surface of the eyeball 500.

Active substances 30 are preferably a medication or drug present in a concentration between approximately 0.1 mg and approximately 10 mg per ml of medium 35, and the medium 35 can have a pH ranging between approximately 6.5 and approximately 8.5.

The medium 35 may also contain supplemental agents, such as electrolytes, stability additives, medicament preserving additives, pH regulating buffers, PEGylating agents, and any other agent that, when associated, shall increase its half-life or bioavailability intraocularly.

The active substances 30 are ionisable by themselves or are in a form that facilitates their ionization. Thus, it is possible to bond active substances to additives presenting terminating ions, such as polymer, dendrimer, polymer nanoparticle or microsphere, or liposome (the active substance is then contained in the aqueous core and not in the wall of the liposome). Various other examples of techniques for improving active substances ionization should also be found in "Progress in retinal and eye research" from Le Bourlais et al. (Vol 17, No 1, p 33-58, 1998; "Ophthalmic drug delivery systems—recent advances"), in "Recent developments in ophthalmic drug delivery" from Ding (PSTT Vol. 1, No. 8 November 1998) and in "European Journal of Pharmaceutics and Biopharmaceutics" from Lallemand et al. (2003, <<Cyclosporine A delivery to the eye: A pharmaceutical challenge").

The passive electrode 40 may be placed at the vicinity of the active electrode 10 (in order to "loop" current through the body), for example on an ear, on the forehead, on the neck, or on a cheek. As with active electrode 10, passive electrode 40 may comprise an anode or a cathode depending upon whether the active substances 30 are cationic or anionic.

The hollow body 21 of the reservoir 20 is opened on an application surface 2 intended to receive a determine part of the eyeball 500 surface.

The application surface 2 is at least partly limited by a convex curved outer line 4 from which the outer wall 24 divergently extends (see also FIG. 3).

Optionally, this outer line 4 can be substantially an arc of circle, a loop like a circle.

The outer wall 24 may be designed for having a substantially constant inclination angle "α" from the optical axis 1 of the eyeball 500. The outer wall 24 delimits a tapered-shape with a cross-section which progressively increases if going away from the application surface 2.

Optionally, the application surface 2 is also at least partly limited by an inner line 5 from which an inner wall 26 extends (see FIG. 4). This inner line 5 can be substantially concave curved, like an arc of circle, a loop, or a circle.

The inner wall 26 extends from the inner line 5 convergently, parallelly to or divergently with respect to optical axis 1. The inner wall 26 may be designed for having a substantially constant inclination angle "β" from the optical axis 1.

Figure 2A:
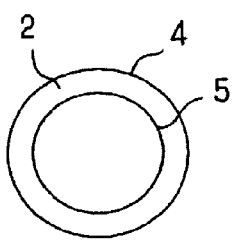
FIGS. 2A to 2E show various shapes and areas of surfaces of application of devices onto an eye, according to the invention.
Figure 2B:
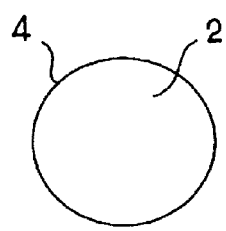
Figure 2C:
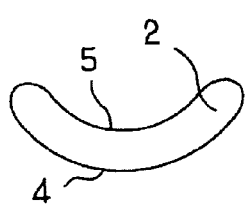
Figure 2D:
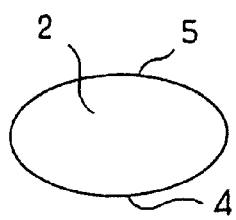
Figure 2E:
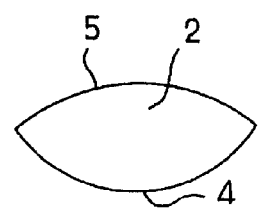

FIGS. 2A to 2E show particular shapes which may be given to an application surface 2 of the reservoir 20, such as an entire ring (FIG. 2A), a disk shape (FIG. 2B), a shape constituting a portion of a ring (FIG. 2C), an ellipse shape (FIG. 2D), or an eye-shape (FIG. 2E). Other shapes can be chosen depending on the ocular area chosen for receiving the active substances 30. These different shapes should be close to or greater than the shape and the area of the ocular surface to be treated. In a particular case, these shapes reproduce the ocular surface to be treated.

The reservoir 20 is also limited at its bottom by a surface 3, adjacent to the electrode 10.

The wall(s) of the reservoir 20 is (are) made of an electrically insulating material, such as plastics material, silicone material, polymer, or any other equivalent material.

FIG. 3 shows a perspective view of a reservoir 20 without inner wall 26, having a tapered shape around the said optical axis 1.

FIG. 4 shows a perspective view of a reservoir 20 with an inner wall 26 and an outer wall 24 having each a tapered shape, divergent from the optical axis 1 by, respectively, an angle "β" and angle "α". The hollow body 21 is then located between the inner wall 26 and the outer wall 24.

Alternatively, the reservoir 20 is defined as a portion of the said tapered shape. This portion can be firstly found by transversally cutting the reservoir 20 of FIG. 4 in two portion (as illustrated in FIG. 4: cuts are along surfaces 101 and 102). Secondly, some additional walls are then provided along the cut surfaces 101 and 102, for closing one of the two portions. For example, a reservoir 20 having an application surface 2 as shown in FIG. 2C is obtained.

Alternatively, this last reservoir 20 can be obtained by integrally moulding it.

The shape and the area of the said application surface 2 to be covered by the eyeball 500 surface can be determinate by the limits of accessibility of the reservoir and the nature of the intraocular tissue to be treated.

Thus, it can be chosen the largest application surface 2 for delivering the active substances 30 to intraocular tissues, in order to maximise the distribution of the active substances 30 on a part of the eyeball 500 that can be useful for the administration of active substances 30.

Alternatively, it can be chosen a limited application surface 2 for delivering the active substances 30 to special intraocular tissues, in order to optimise the administration of active substances 30 in this part of the eyeball 500, and thus limiting the loss of substances 30 and maximising the concentration of active substances 30 inside the ocular tissues to be treated. Then, the administration of the product is precisely targeted to intraocular tissues while avoiding systemic absorption.

For example, if the affected tissues are located in Cornea or in Iris, the application surface 2 can be chosen for receiving the whole Cornea 501, eventually extended to the periphery of the sclera 502, in order to administer active substances 30 to the ciliary body that may be an additional path for reaching Iris.

Eventually, a removal of the anterior corneal epithelium can be previously operated for making the remained corneal tissues (i.e. stroma and posterior corneal epithelium) more permeable to the active substances 30.

In another example, if the affected tissues are located in Retina or in Choroid, the chosen ocular area on the surface of the eyeball 500 intended to receive the active substances 30 from the reservoir 20 can be the whole part of the sclera 502 that is accessible to active substances 30, eventually extended to the part of the sclera located under eyelids.

The reservoir 20 of the device may then be adapted to administer the active substances 30 via:

at least a part of the cornea 501 alone; or at least a part of the sclera 502 and at least a part of the cornea 501; or at least a part of the sclera 502 alone.

The cornea 501 constitutes about 5% of the total area of the eye and joins the sclera 502 at the limbus 503. In the human being, the diameter of limbus 503 is about 11.7 mm.

In a preferred embodiment of the invention, the device is arranged so as to dispense the active substances 30 through at least a part of the sclera 502 for reaching determinate targeted tissues, the cornea 501 being a portion of the eye that is much more critical than the sclera 502.

Additionally, sclera 502 is much more permeable to large particles than cornea 501.

The volume and the shape given to the hollow body 21 (defining a space filled by the medium 35 and the active principles 30) are designed for allowing the electric field (supplied by the active electrode 10) to be guided from the electrode 10 to the said application surface 2 so that ionized active principles 30 reach a determine target ocular tissue with an improved efficiency and increased concentration.

For example, referring to FIG. 5, a device according to those of FIG. 3 is shown in operation, this device having a reservoir 20 containing an electrical conductive solution or gel 35 capable of conducting the electric field E supplied by an active electrode 10. This electrical conductive medium 35 can be for example an aqueous solution or a hydrogel.

The reservoir 20 is tapered around the optical axis 1 of the eyeball 500 so that the section of its hollow body 21 progressively decreases when approaching the eyeball 500. As the active electrode 10 is in a disk-shape, eventually curved, and has substantially the same area as the bottom surface 3 of the reservoir 20, the active electrode 10 area "Se" is then greater than the application surface 2 area "Sa".

Accordingly, since the force applied by the electric field E generated by the electrode 10 onto the ionized substance 30 contained in the reservoir 20 is defined by Coulomb's law and depends on the charge and the field intensity, the charge and the speediness of the ionized substances 30 are increased, in comparison with those of a cylindrical reservoir having the same length "L" and the same "Sa" as it is known from the prior art.

The field's intensity is then increased by a value proportionate to the ratio "Se/Sa", and will lead to a reduction of the residence time of the device on the eye for the same delivery of active substances 30, or to a more important amount of delivered active substances 30 for the same application time, than in a known iontophoresis device.

Furthermore, the length "L" of the reservoir 20 is chosen sufficiently high so that the chosen medium 35 guides the electric field E from the electrode 10 to the application surface 2 for obtaining a substantially increasing flux along the section of the hollow body 21, and for having, at the eyeball surface 500, an electric field E globally straight and convergent, with few or no leaking current, particularly at the contact points between the reservoir wall 24 and the ocular surface, and for not exceeding a current-limit at the application surface 2 beyond which the eyeball 500 could be damaged.

Thus, the reservoir 20 can be arranged so that active electrode 10 is distant from the application surface 2 of the reservoir 20 facing the eyeball 500 of about or greater than 3 times the longest linear dimension of "Sa".

The concentration of active substances 30 in the intraocular tissues is then increased and optimised by using the device according to the invention.

Referring to FIG. 6, the same principle can be used for the device according to FIG. 4, whose the application surface 2 is here annular around the optical axis 1 and the tapered inner wall 26 extending from the inner loop of the application surface 2 is divergent from an inclination angle "β" lower than the inclination angle "α" of the outer wall 24 divergently extending from the outer loop of the application surface 2.

As the active electrode 10 is in an annular-shape and have substantially the same area as the annular bottom surface 3 of the reservoir 20, the active electrode area "Se" is then greater than the application surface area "Sa".

The same effects and results as those previously described referring to FIG. 5 are then observed in the reservoir 20, for the intraocular tissues facing the annular application surface 2.

In another embodiment of the invention, FIG. 7 shows a particular device for delivering some active substances into ciliary body 510, for treating for example problems of glaucoma as previously explained.

The device has, in operation, an annular application surface 2 around the optical axis 1, a tapered inner wall 26 extending from the inner loop of the application surface 2, a tapered outer wall 24 extending from the outer loop of the application surface 2, both walls 24-26 being globally divergent of a same inclination angle "α" respective to the optical axis 1.

Then the whole reservoir 20 can be considered here as being inclined by an angle "α" respective to the optical axis 1, and the hollow body 21 having a substantially constant section.

The inner diameter "di" of the inner loop of the application surface 2 and the outer diameter "do" of the outer loop of the application surface 2 are chosen so that the application surface 2 is in front of the ciliary body 510 (in projection).

It can be observed that the eyeball 500 schematically shown here comprised the cornea 501, the sclera 502, the lens 504, the Iris 508, the ciliary body 510, the choroids 505, the retina 506 and the optical nerve 507.

The ciliary body 510 is composed of the anterior pars plicata ciliaris 511 (or "pars plicata") and the posterior pars plana ciliaris 512 (or "pars plana").

The pars plicata 511 is about 2.5 mm in anteroposterior dimension and contains the muscles of the ciliary body 510.

The pars plana 512 is about 3 mm wide nasally and about 4.5 temporally and extends from the pars plicata 511 to a region close to the beginning of the anterior segment of the retina 506.

Referring to FIG. 7, the device is designed for specially treating the pars plicata 511, having an application surface 2 with a "di" of about 12 mm and a "do" of about 16 mm, giving a reservoir 20 of about 2 mm width.

Alternatively, "di" is of about 12 mm and a "do" is of about 21 mm, giving a reservoir 20 of about 4.5 mm width, for treating the whole ciliary body 510.

The active electrode 10 is annular and has an area which is substantially the same as the bottom 3 of the reservoir 20, perpendicular to the outer wall 24 and to the inner wall 26.

It is to be noticed that:

$(D_e - D_i) \approx (d_e - d_i)$, if $D_e$ is the outer diameter and $D_i$ is the inner diameter of the active electrode 30; and $(D_e + D_i) > (d_e + d_e)$ ⇒ Then, $(D_e - D_i)(D_e + D_i) > (d_e - d_i)(d_e + d_i)$ Accordingly:

$$\frac{\Pi}{4}(D_e^2 - D_i^2) > \frac{\Pi}{4}(d_e^2 - d_i^2)$$

Then, the device of FIG. 7 includes an active electrode 30 having an area greater than the area of the application surface 2.

The angle "α" is chosen for being applied to the ciliary body 510, so that the reservoir 20 is substantially perpendicular to the local eye surface. This angle "α" can then be chosen between around 30° and around 40°.

Accordingly, the electric field and current lines are substantially directed perpendicularly to the ciliary body 510, and the concentration of active substances 30 in the plars plicata 511 is then optimised, if the intensity of the current is adapted.

In order to treat problems of glaucoma by iontophoresis treatment of ciliary body 510, the following active substances 30 can be used:

Beta blockers: betaxolol, levobunolol, timolol, carteolol befunolol, metipranolol Alpha adrenergic agonists: brimonidine, apraclonidine, dipivefrine Carbonic anhydrase inhibitors: dorzololamide, brinzolamide, acetazolamide, methazolamide Non-specific Adrenergic agonists or sympathomimetic agents: epinephrine, phenylephrine, dipevefrin, apraclonidine Cholinergic agonists (anticholinesterase agents) or parasympathomimetics: pilocarpine, carbachol, aceclidine, echothiopathe Prostaglandin analogues: latanoprost, bimatoprost, travoprost.

These pharmacological approaches help restore the IOP to a normotensive state either by inhibiting the production of aqueous humor by the ciliary body 510 (for the three first substances), or facilitating trabecular or uveoscieral aqueous humor outflow (for the three last substances).

Figure 8:
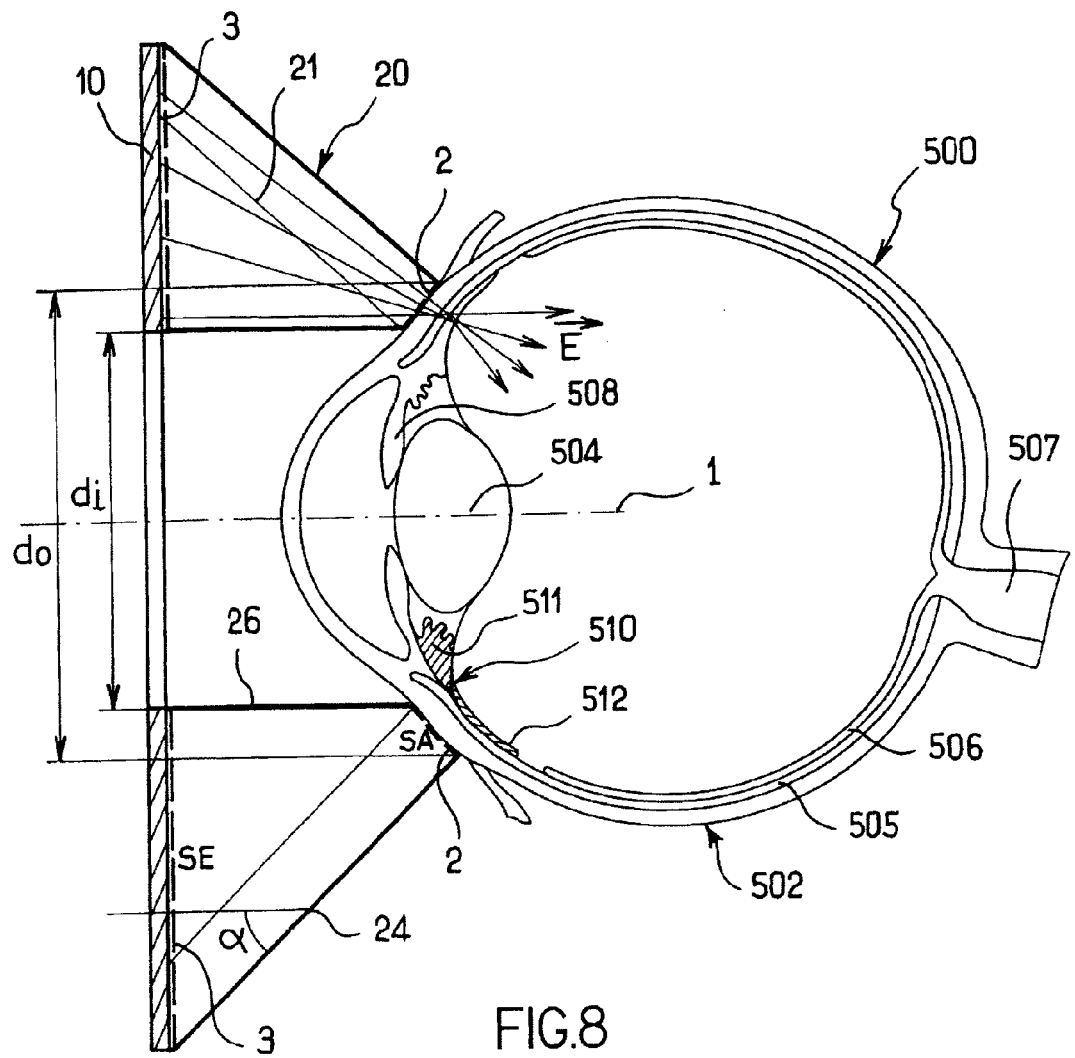
FIG. 8 shows a longitudinal cross section of another particular device according to the second embodiment once applied on the eyeball.

FIG. 8 shows another device for delivering some active substances into ciliary body 510, for treating for example problems of glaucoma as previously explained.

This device has, in operation, an annular application surface 2 around the optical axis 1 of the eyeball 500, a cylindrical inner wall 26 extending from the inner loop of the application surface 2, a tapered outer wall 24 extending divergently from the outer loop of the application surface 2 with an inclination angle "α" respective to the optical axis 1.

Then the hollow body 21 has a section which progressively increases from the surface of the eyeball 500, as already described referring to FIG. 6.

The active electrode 10 has an annular shape, and has substantially the same area as the annular bottom surface 3 of the reservoir 20.

Accordingly, the active electrode 10 area "Se" is then greater than the application surface 2 area "Sa".

Additionally, the active electrode 10 can have a surface perpendicular to the outer wall 24 or to the inner wall 26. Its location can also be chosen parallel to the application surface 2.

The inner diameter "di" of the inner loop of the application surface 2 and the outer diameter "do" of the outer loop of the application surface 2 can be chosen so that the application surface 2 is in front of the ciliary body 510 (in projection).

The device is designed here for treating more specifically the pars plana ciliaris 512, with a reservoir 20 having a "di" of about 17 mm and a "do" of about 21 mm, giving an application surface 2 of about 2 mm width.

Alternatively, "di" is of about 12 mm and a "do" is of about 16 mm, giving a reservoir 20 of about 2 mm width, for treating pars plicata 511.

The angle "α" of the outer wall 24 is chosen so that the latter is substantially perpendicular to the ciliary body 510. This angle "α" can then be chosen between around 30° and around 40°.

With this configuration, the electric current is directed more perpendicularly to the pars plana 512, and has a greater intensity as previously explained referring to FIG. 6.

With reference to FIG. 9, a particular annular ocular iontophoresis device according to the invention is shown. It comprises an active electrode 10 with a through opening so as to provide an annular structure, and placed at the bottom 3 of the reservoir 20, which is also annular in section.

As previously explained, the reservoir 20 extends along an application surface 2 intended to cover a determinate ocular area of the eyeball 500. The ocular area intended to receive active substances 30 from the device 1 is at least a part of the sclera 502, as described here-below, and in particular the ciliary body 510 or a part of it.

The hollow body 21 of the reservoir 20 is here divided in two parts:

a first container 23 placed at the front part of the reservoir 20 (the front part being the closest part from the eyeball 500) delimited by a front part 24b of the outer wall 24 and a front part 26b of the inner wall 26;

a second container 22 placed at the bottom part of the reservoir 20 delimited by the rear part 24a of the outer wall 24 and the rear part 26a of the inner wall 26.

The first container 23 is intended to receive the medium 35 containing the active substances 30, and the second container 22 is intended to receive an electrically conductive medium 37 like an aqueous solution or a hydrogel. The first and second containers 23-22 are separated by a semi-permeable membrane 80 permeable to electrical conductive elements contained in the medium 37 and non-permeable to active substances 30 of the first container 23.

The medium 35 can then be limited in thickness to reduce the active substances 30 volume to the minimal, and to permit a precise dosage of its content, improving the control upon the iontophoresis and the cost of it.

Preferably, the inner wall 24 and outer wall 26 extend from the surface of the electrode 10 so as to define between them a hollow body 21 (i.e. the second container 22 and the first container 21) which has an annular section progressively decreasing when approaching the application surface 2.

Furthermore, the length of the second container 22 is preferably chosen sufficiently long so that the electrical conductive medium 37 provided herein guides the electric field from the active electrode 10 through the first container 23 to the application surface 2 with straight electric field. Leaking currents are then limited.

As previously explained, the length of the hollow body 21 can be chosen to be close to or greater than 3 times the longest linear dimension of the said reservoir surface.

The application surface 2 optionally presents a mean inside diameter $d_i$ such that $D<d_i\leq 1.2D$, D being the diameter of a cornea 501.

In such case, iontophoresis principally takes place through the sclera 502.

The application surface 2 optionally presents a mean outside diameter $d_e$ where $1.3D<d_e\leq 1.8D$.

The global angle of inclination of the outer diameter 24 relative to the optical axis 1: may be included in the range from 10° to 80°, and especially between around 30° and around 40°.

The global angle of inclination of the inner diameter 26 relative to the optical axis 1 may be included in the range of 0° to 80°, and especially between around 30° and around 40°.

One end of the rear outer wall 24a may be connected to one end of the rear inner wall 26a by a transverse wall for forming a bottom wall of the second container 22 (not shown). The active electrode 10 is then positioned or formed on said end wall.

In a variant, the active electrode 10 is positioned or formed for closing the rear walls 24a and 26a of the second container 22 in such a manner as to constitute the end wall of the reservoir 20 (as shown in FIG. 7).

In anyway, the reservoir 20 can be designed so that its bottom 3 part has an area greater than those of the application surface 2. Then, the area "Se" of the active electrode 10 is greater than the area "Sa" of the application surface 2, involving the advantages previously discussed.

The active electrode 10 optionally includes an offset portion 15 enabling the connection 50 with a wire link 60 that supplies electricity to be offset out from the reservoir 20 when connected to a suitable electrical power supply (not shown), one end of the offset part 15 being electrically connected to the electrode layer 10, while the other end of the offset part receives the wire link 60. Thereby harmful effects that might arise from the electrical connection can be avoided (local heating by Joule effect, local leakage currents, . . . ).

In addition, the device has a rear portion 70 that is sufficiently reinforced or rigid for holding the whole device when placed on the eyeball 500 without significantly deforming the reservoir 20, and for maintaining the geometry of the active electrode 10.

Eventually, the active electrode 10 is concave, in order to be substantially parallel to the application surface 2.

In this case, the active electrode 10 is interposed between the rear portion 70 and the reservoir 20, resting against the rigid rear portion 70.

Thus, when the reservoir 20 is in position, the distance between the surface of the active electrode 10 and the surface of the eyeball 500 can be maintained more or less constant in spite of the mechanical stresses exerted by the eyelids and by the hand of the user.

The ring formed by the active electrode 10 can keep its shape under the pressure exerted by the eyelids and by the user, thereby maintaining the distance between the active electrode 10 and the application surface 2 greater than a limit distance, in order to prevent any damage of the ocular tissue due to the electric field. Thus, this limit distance can be chosen about 4 mm from the application surface 2, (as previously described), since otherwise there would be a danger of a short-circuit by favourable lines of current being established between the active electrode 10 and the ocular tissues.

Front outer wall 24b and front inner wall 26b are of a flexible material for acting as a barrier against outer contaminants and lacrymal liquid that might disturb the operation of the device (arc effect).

The free end of the front inner side wall 26b is optionally slightly offset relative to the free end of the front outer side wall 24b such that the opening of the reservoir 20 (between these free ends) defines an application surface 2 that is globally complementary in shape to the convex curved shape of the surface of the eyeball 500.

The flexible part of the front side walls 24b and 26b may be made of silicone of the polydimethyl siloxane type (PDMS), a material that is highly suitable for making contact with the eyeball 500.

However its flexibility certainly does not enable it to keep its shape in geometrically accurate manner.

That is why it is appropriate to provide rigid or reinforced rear portion 24a, 26a, 70 (and eventually a rear part of the front walls 24b and 26b) to make them in a material such as, for example, polymethyl methacrylate (PMMA), or any rigid polymer material with a specific resistance (elastic modulus/ weight ratio) appropriate to maintain its initial shape under mechanical constraint.

PMMA is a rigid material suitable for keeping the active electrode 10 in shape. However it is unsuitable for making the front walls 24b and 26b intended to be brought into contact with the eyeball 500 (it is a material that is too traumatic for the delicate mucus membrane of the eye).

These two materials in combination thus provide a device structure that is entirely suitable for ocular iontophoresis.

The rigid portion 70 and the rear inner and outer walls 24a-26a of the reservoir 20 can be made, for example, by machining, moulding, vacuum casting, or any other method suitable for working polymer materials of rigid or semi-rigid kind such as polystyrene (PS), acrylonitrile-butadiene-styrene (ABS), polyethylene (PE), polypropylene (PP), polyamide (PA), polycarbonate (PC), PMMA, polyurethane (PUR).

During fabrication of the part, provision can be made to mould means for filling the reservoir 20 with active substances 30 and/or means for circulating the active substances 30 in the reservoir 20. For example, tubes for feeding of or circulating active substances 30, and optionally outlet tubes may be provided (not shown).

The active electrode 10 can be deposited on the surface of the bottom 3 of the reservoir 20, using for example one of the methods mentioned above.

Finally, the flexible front walls 24b-26b can be made of a polymer material such as, for example, an elastomer polymer of the PUR type, polyether block amide (PEBA), silicone (SI), or styrene-ethylene-butadiene-styrene (SEBS), and it may be fitted to the assembly using any suitable method, for example adhesive, heat sealing (e.g. by ultrasound, or by rotation, or by mirror), or by overmolding.

The flexible front walls 24b-26b of the reservoir 20 may also be made by successively adding sections of material of progressively-varying hardness, from the thickest to the thinnest and from the stiffest to the most flexible, so as to make a reservoir of stiffness that increases progressively going away from the application surface 2 (see below, and FIGS. 10A-10C).

The inside walls of the reservoir 20 are optionally provided in the reservoir 20 for defining compartments, the active electrode 10 then being subdivided into active electrode portions, each active electrode portion being suitable for being placed in its own compartment. Specific treatments can then be performed using different active substances 30, each occupying a different compartment, and administered simultaneously or in deferred manner (in which case each electrode portion has its own current control). Advantageously, filling and/or circulation means for medication 30 are provided in each compartment.

With reference to FIGS. 10A to 10C, several examples of front walls 24b-26b are shown, each having a section that becomes progressively larger and larger on going away from the application surface 2.

With reference to FIG. 10A, the front wall 24b-26b forms a ramp sloping progressively away from the application surface 2 of the reservoir 20 until having the thickness of the rigid rear side wall 24a-26a.

With reference to FIG. 10B, the front wall 24b-26b formed is a lip of section that increases going away from the application surface 2 of the reservoir 20, and of sides that are concave.

With reference to FIG. 10C, the front wall 24b-26b is constituted by successive layers of ever increasing section (on going away from the application surface 2 of the reservoir 20). These various layers may optionally be of ever increasing hardness.

Figure 11:
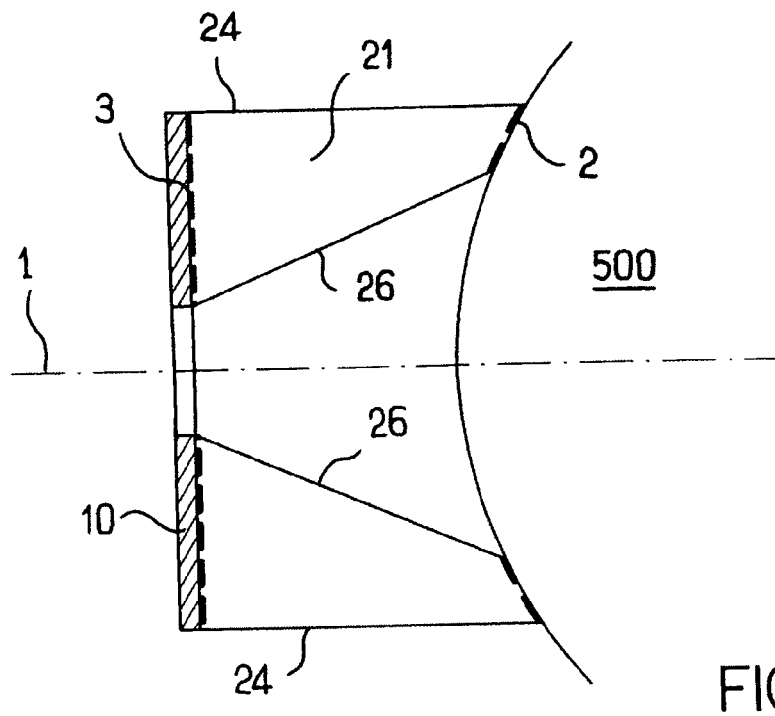
FIGS. 11 and 12 show respectively two kinds of device according to a third embodiment of device according to the invention.
Figure 12:
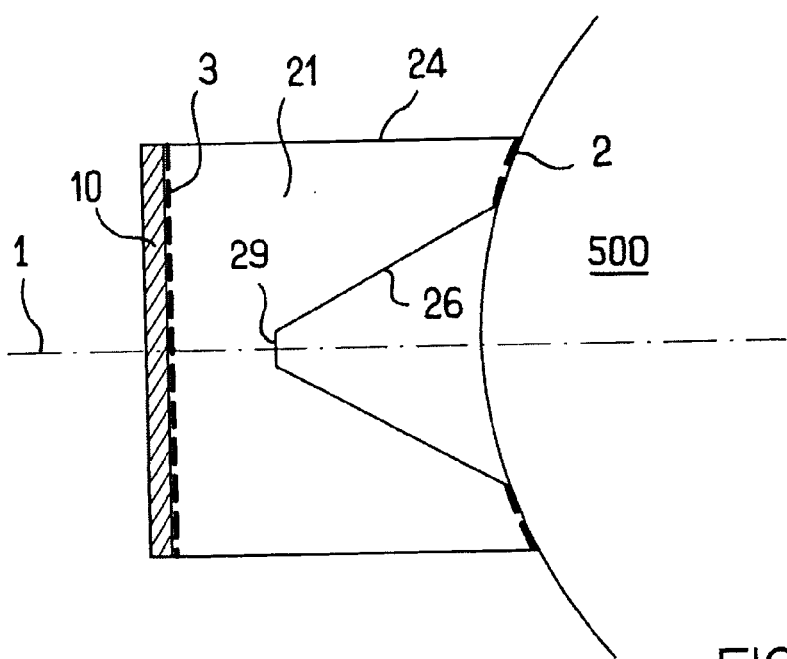

The active electrode 10 may be parallel to the cylindrical outer wall 24 (as shown in FIGS. 11 and 12) or may be deflected in a concave manner respectively to the convex eyeball surface (not shown). In this last case, the deflection of the active electrode 10 can be chosen for ensuring a global equidistance between the active electrode 10 and the surface of the eyeball 500.

Referring to FIGS. 11 and 12, another embodiment of a iontophoresis device according to the invention is shown, wherein the cross-section of the hollow body 21 of the reservoir 20 increases form the application surface 2 due to an inclination of the inner wall 26 with respect to the optical axis 1 of the eyeball 500, while the outer wall 24 is globally cylindrical. The inclination of the inner wall 26 is chosen such that this inner wall 26 is convergently tapered if going away from the eyeball 500.

Referring to FIG. 11, the inner wall 26 contacts the bottom 3 of the reservoir 20. The cross-section of the hollow body 21 is then entirely annular all along the optical axis 1.

Alternatively, referring to FIG. 12, the inner wall 26 is jointed at one point or at one surface 29 and does not contact the bottom 3 of the reservoir 20. The cross-section of the hollow body 21 is then annular in a region from this point or surface junction 29 to the application surface 2, and has a disk-shape in the region from this point or surface junction 29 to the bottom surface 3 of the reservoir 20.

This other embodiment of a iontophoresis device according to the invention leads to an area "Se" of the active electrode 10 greater than the area "Sa" of the application surface 2. This involves the advantages previously discussed.

Tests n° 1:

The assignee made some comparative tests on rabbits done with a iontophoresis device as shown in FIG. 7 (i.e. the inner wall 26 and outer wall 24 being tapered with the same inclination angle of about 35° for treating the ciliary body) and with topical means (typically the administration of some drops with drug on one eye).

For each comparative test, the medium 35 used (water) and the active substances 30 administrated ($^3$H-clonidine) were the same with a substantially identical concentration (0.25% w/v for the active substance 30, i.e. in grams of substance 30 contained in 100 ml of solution).

Topical conditions were 0.05 ml on one eye.

Iontophoresis conditions were a current intensity of about 2 mA supplied for about 4 minutes. The device contained 0.5 ml of solution.

Rabbits ocular tissues were then sampled 0.5 hour, 1 hour and 6 hours after the active substances 30 been administered. Tissues sampled included ciliary body.

Concentrations of active substances 30 in these ocular tissues were then measured by radioactive emission of the active substance 30 previously radio-marked. The measurement unit is in ng/g of tissue. Results are given in table 1.

TABLE 1

| Tissue | Time (h) | Ionto.- 0 mA (ng/g) | Ionto.- 2 mA (ng/g) | Topic (ng/g) | Ratio ionto (0 mA)/topic | Ratio ionto (2 mA)/topic |
|---|---|---|---|---|---|---|
| Ciliary body | 0.5 | 15612 | 84034 | 10587 | 1.5 | 7.9 |
| Ciliary body | 1 | 17064 | 82711 | 15714 | 1.1 | 5.3 |
| Ciliary body | 6 | 14907 | 41716 | 12767 | 1.2 | 3.3 |

It is to be noticed that, without current, iontophoresis (0 mA) has about the same efficiency as the topic administration (regarding the margin of error of each one of these two techniques). In operation, the conditions can then be considered as similar one to each other.

Nevertheless, at least three times more active substances 30 were found in the ciliary body 510 when using the iontophoresis device with 2 mA applied, in comparison with results when using the topical method.

Accordingly, the iontophoresis technique of the invention is clearly more efficient than the topical method, for treating the ciliary body 510, and should then give better results for the treatment of glaucoma.

Tests n° 2:

The assignee made some comparative tests on rabbits done with a first iontophoresis device having cylindrical outer and inner walls (as known in the prior art) and a second iontophoresis device as shown in FIG. 7 (i.e. the inner wall 26 and outer wall 24 being tapered with the same inclination angle).

The two devices were designed for having the same:
application surface 2;
distance between the active electrode 10 and the application surface 2.

The area of the active electrode 30 of the second device was about three times more important than those of the first device.

Additionally, for each comparative test, the medium 35 used (water with no buffer) and the active substances 30 administrated (Dexamethasone Disodium Phosphate) were the same with a substantially identical concentration (40 mg/ml for the active substances 30).

For each comparative test, iontophoresis conditions were the same (2 mA—4 min).

After iontophoresis, rabbit ocular tissues were sampled. Tissues sampled included choroids and retina.

Concentrations of active substances 30 in these ocular tissues were then measured.

At least three times more active substances 30 in the tissues were found when using the second device, in comparison with results when using the first device.

In particular, the increase concentration tissues were 3.7 for the choroids and 3.4 for the retina.

Accordingly, the second device is clearly superior to the first one.

These main improvements can only be explained by the increase of the area of the active electrode 30 between the first and second device (area was multiplied by about three).

The invention claimed is:

1. An ocular iontophoresis device for delivering active substances to an eyeball, the ocular iontophoresis device comprising:
an active electrode;
a reservoir having an inlet comprising a rigid material for maintaining a shape of the active electrode and an outlet comprising a flexible material suitable for making contact with the eyeball, the inlet and the outlet each having a respective diameter, wherein the diameter of the inlet is greater than the diameter of the outlet; and
wherein the outlet defines an application surface adapted to receive a predetermined part of an eyeball surface, wherein an area of the active electrode ("Se") is greater than an area of the application surface ("Sa") to provide an increased electric field intensity by a value proportionate to the ratio "Se/Sa".

2. The ocular iontophoresis device of claim 1, wherein the application surface is designed for covering at least a portion of the cornea of the eyeball.

3. The ocular iontophoresis device of claim 1, wherein the application surface is designed for covering at least a portion of the cornea of the eyeball and at least a portion of the sclera of the eyeball.

4. An ocular iontophoresis device according to claim 1, wherein the reservoir comprises: a first container for containing active substances and the electrically conductive medium;

and a second container for containing electrically conductive elements; wherein the first and second containers are separated by a semi-permeable membrane permeable to the electrically conductive elements and non-permeable to the active substances.

5. The ocular iontophoresis device of claim 1, further comprising an electrically conductive medium contained in the reservoir, wherein the electrically conductive medium is selected from the group consisting of an electrically conductive liquid and a gel.

6. The ocular iontophoresis device of claim 1, wherein the active electrode has globally the same shape as the bottom of the hollow body.

7. The ocular iontophoresis device of claim 1, wherein the active electrode includes a through opening.

8. The ocular iontophoresis device of claim 1, further comprising active substances contained in the reservoir.

9. The ocular iontophoresis device of claim 8, wherein the active substances comprising a medication, a drug, or any combination thereof.

10. The ocular iontophoresis device of claim 1, further comprising an exterior wall and an interior wall, the exterior wall and the interior wall define the reservoir.

11. The ocular iontophoresis device of claim 10, wherein the application surface is designed for covering at least a portion of the sclera of the eyeball.

12. The ocular iontophoresis device of claim 11, wherein the application surface is designed for covering in projection at least a portion of the ciliary body of the eyeball.

13. The ocular iontophoresis device of claim 12, wherein the application surface is designed for covering in projection at least a portion of the anterior pars plicata ciliaris of the eyeball.

14. The ocular iontophoresis device of claim 12, wherein the application surface is designed for covering in projection at least a portion of the posterior pars plana ciliaris of the eyeball.

15. The ocular iontophoresis device of claim 10, wherein the reservoir further comprising:
   at least two compartments for containing different active substances; and
   wherein the active electrode is subdivided into at least two active electrode portions, each respective active electrode portion disposed in the respective compartment of the at least two compartments.

16. The ocular iontophoresis device of claim 10, wherein the application surface is designed for covering at least a portion of the cornea of the eyeball and at least a portion of the sclera of the eyeball.

* * * * *